US00PP28998P3

(12) United States Plant Patent
Ranney

(10) Patent No.: US PP28,998 P3
(45) Date of Patent: Feb. 27, 2018

(54) EVERGREEN DOGWOOD PLANT NAMED 'NCCE1'

(50) Latin Name: *Cornus elliptica*
Varietal Denomination: NCCE1

(71) Applicant: North Carolina State University, Raleigh, NC (US)

(72) Inventor: Thomas G. Ranney, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 14/999,639

(22) Filed: Jun. 8, 2016

(65) Prior Publication Data

US 2017/0359929 P1 Dec. 14, 2017

(51) Int. Cl.
*A01H 5/00* (2006.01)
*A01H 5/02* (2006.01)
*A01H 5/04* (2006.01)

(52) U.S. Cl.
USPC ..... Plt./220
CPC ..... *A01H 5/02* (2013.01); *A01H 5/04* (2013.01)

(58) Field of Classification Search
USPC ..... Plt./220
CPC ..... A01H 5/02; A01H 5/00
See application file for complete search history.

*Primary Examiner* — June Hwu
(74) *Attorney, Agent, or Firm* — Myers Bigel, P.A.

(57) ABSTRACT

'NCCE1' is a new cultivar of evergreen dogwood with an upright, pyramidal habit, dense branching, large showy white bracts, and greyed-purple-colored winter foliage.

3 Drawing Sheets

Latin name of the genus and species: The Latin name of the novel plant variety disclosed herein is *Cornus elliptica.*

Variety denomination: The inventive variety of an open-pollinated *Cornus elliptica* (formerly *C. angustata*) 'Elsbry' (U.S. Plant Pat. No. 14,537) disclosed herein has been given the varietal denomination 'NCCE1'.

BACKGROUND OF THE INVENTION

The present invention comprises a new and distinct dogwood cultivar hereinafter referred to by the cultivar name 'NCCE1'. This new dogwood was developed through a breeding program in Mills River, N.C. 'NCCE1' was selected from a population of seedlings grown from an open-pollinated *Cornus elliptica* 'Elsbry', NCSU 2006-030 (U.S. Plant Pat. No. 14,537). The first asexual propagation of 'NCCE1' was carried out in July 2010 by rooting stem cuttings in Mills River, N.C. and has been asexually reproduced repeatedly by vegetative cuttings and micropropagation from axillary shoots over a 5-year period. 'NCCE1' roots readily from softwood cuttings treated with a basal dip of 4,000-5,000 ppm indole butyric acid (potassium salt) in water. 'NCCE1' has been found to retain its distinctive characteristics through successive asexual propagations.

SUMMARY OF THE INVENTION

The following are the unique combination of characteristics of this new dogwood cultivar when grown under standard horticultural practices in Mills River, N.C.

1. Narrow, upright habit with dense branching.
2. Large, ivory-colored bracts.

3. Evergreen with glossy, greyed-purple-colored, winter foliage.
4. Cold hardy to USDA Zone 6B.

BRIEF DESCRIPTION OF THE DRAWINGS

This new dogwood is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new dogwood.

DETAILED BOTANICAL DESCRIPTION

Figure 1:
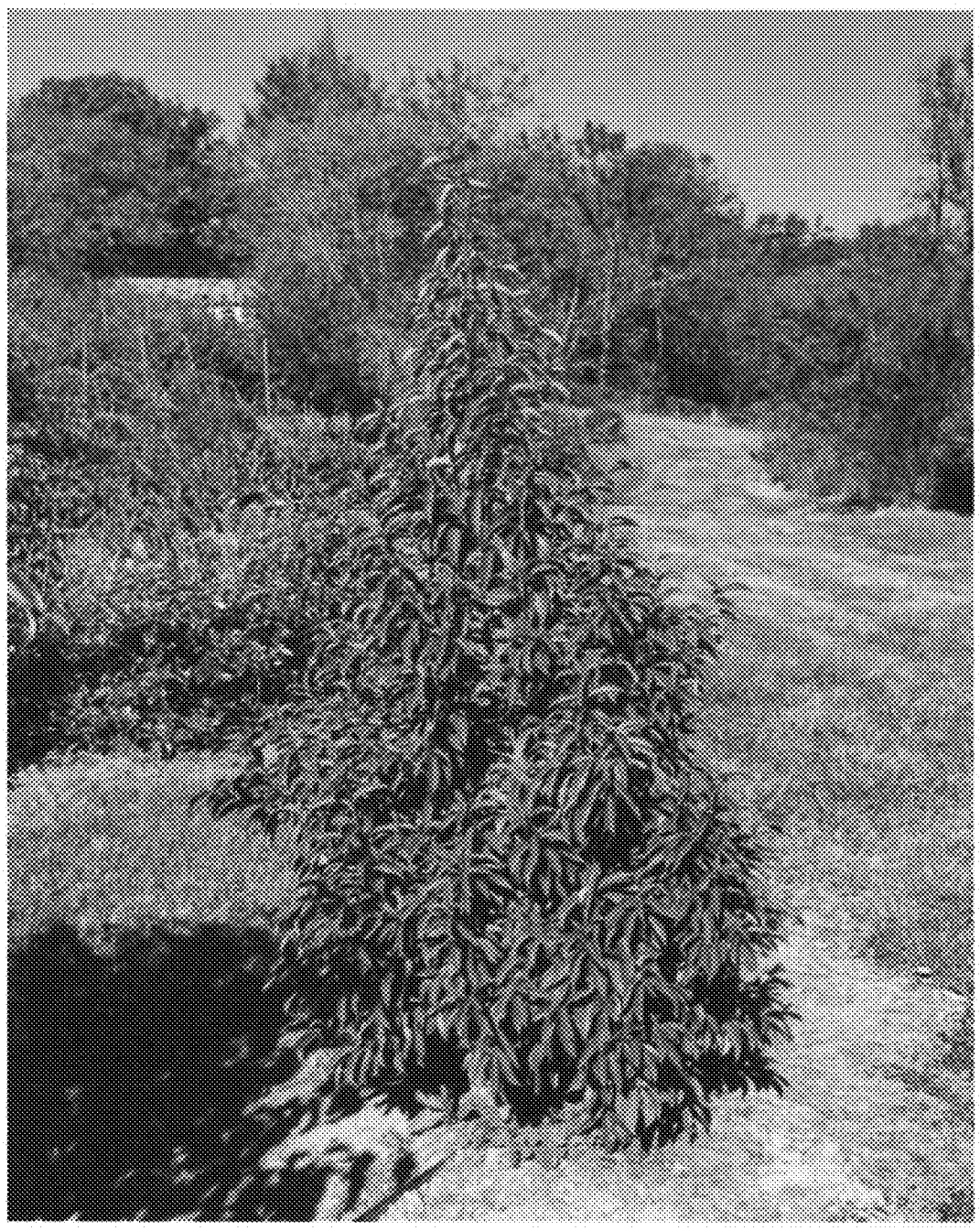
FIG. 1 is a photograph showing upright habit and dense branching of 'NCCE1' taken in July 2012 on a four-year-old, field-grown tree.
Figure 2:
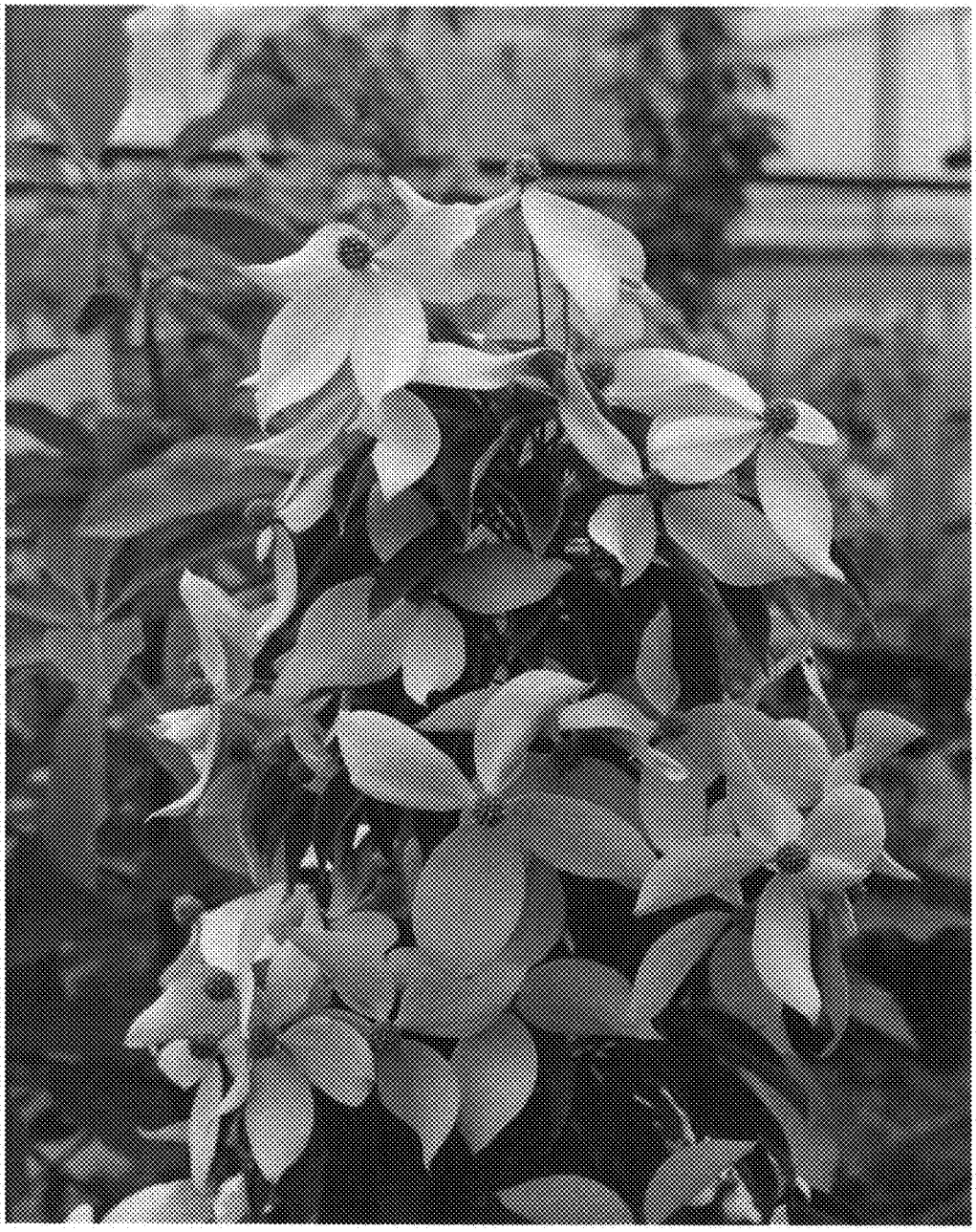
FIG. 2 is a photograph of the inflorescences of 'NCCE1' taken in June 2013 on a four-year-old, container-grown tree.
Figure 3:
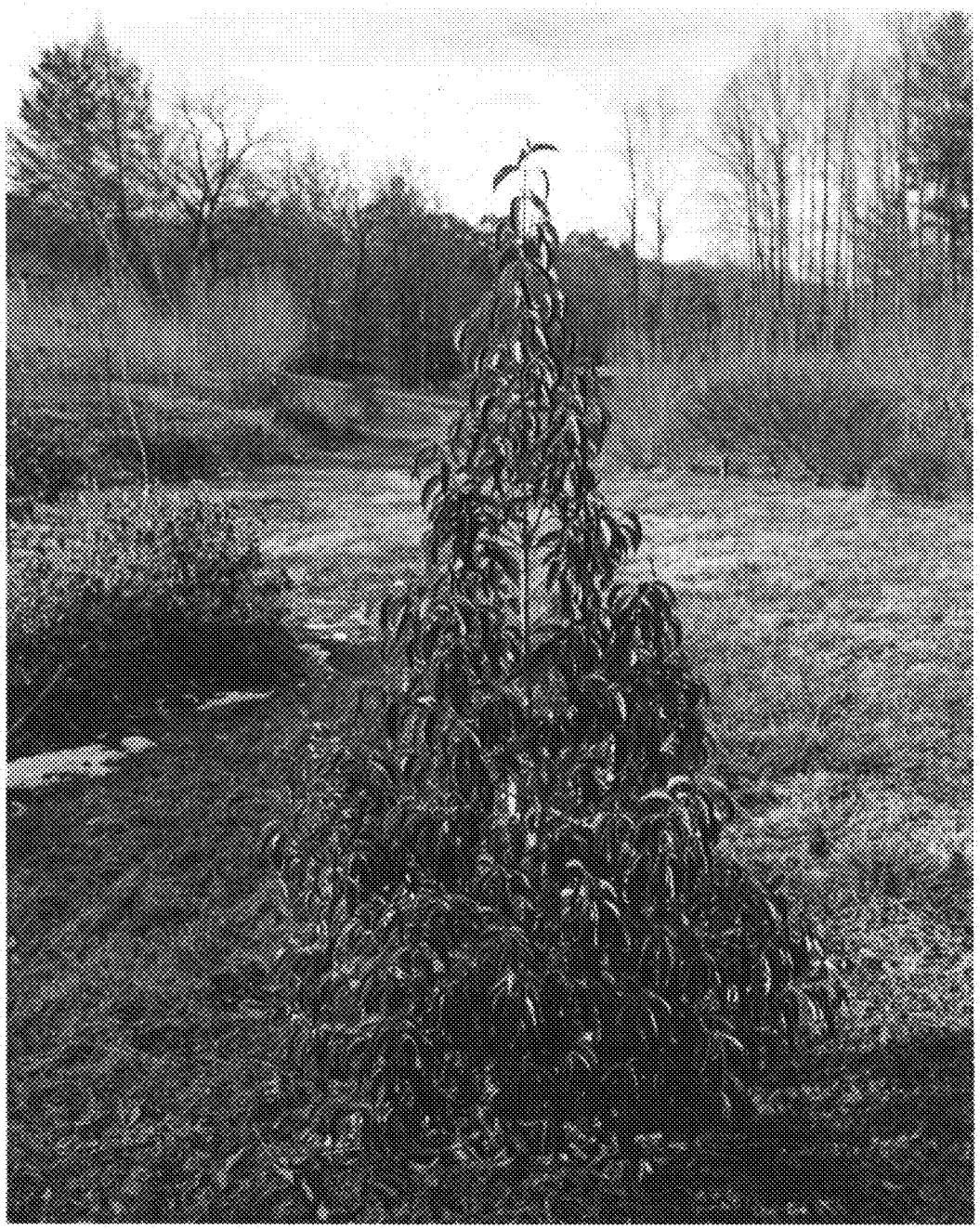
FIG. 3 is a photograph of 'NCCE1' with winter-colored foliage taken in January 2011 on a three-year-old, field-grown tree.

The following is a detailed description of the botanical characteristics of the new and distinct dogwood plant cultivar known by the denomination 'NCCE1'. The detailed description was taken on a six-year-old field-grown plant in Mills River, N.C. in 2014. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Cornus elliptica* 'NCCE1'.

*Common name.*—Evergreen dogwood.

Parentage: Seedling grown from an open-pollinated *Cornus elliptica* 'Elsbry' (U.S. Plant Pat. No. 14,537).

Plant description:

*Growth habit.*—Narrow, pyramidal.

*Height.*—4 m after 6 years.

*Width.*—1-1.3 m at base after 6 years.

Leaves:

*Type.*—Simple.

*Persistence.*—Evergreen to 10° C.

*Arrangement.*—Opposite.

*Shape.*—Elliptical to lanceolate.

*Apex.*—Acuminate.

*Base.*—Cuneate.

*Vein number.*—4-5 vein pairs.

*Venation.*—Pinnate, arcuate.

*Vein color in summer.*—Upper: Yellow-green (RHS 145A). Lower: Yellow-green (RHS 145D).

*Vein texture.*—Pubescent.

*Margins.*—Entire.

*Emerging leaves.*—Color: Upper: Upper: Greyed-green (RHS 197B) with a blush of Grayish-red (RHS 176A) and a Grayish-red margin (RHS 176A). Lower: Yellow-green (RHS 148D). Texture: Upper: Pubescent, glossy. Lower: Pubescent, dull.

*Mature leaves during growing season.*—Color: Upper: Green (RHS 139A). Lower: Greyed-green (RHS 191B). Texture: Upper: Fine pubescence, glossy. Lower: Fine pubescence, dull. Length of lamina: Avg. 10 cm (range 7.5 to 12 cm). Width: Avg. 4 cm (range 2.5 to 4.5 cm).

*Fall and winter foliage color.*—After frost, foliage transitions from green (RHS 139A) to greyed-purple (RHS 183A).

*Leaf attachment.*—Petiolate.

*Petiole.*—Length: Avg. 10 mm (range 5 to 15 mm). Diameter: Avg. 1 mm (range 1 to 1.5 mm). Color: Yellow-green (RHS 145B). Texture: Pubescent.

*Vegetative bud.*—Shape: Lanceolate, acuminate. Length: Avg. 4 mm (range 3 to 6 mm). Texture: Pubescent. Color: Yellow-green (RHS 148C).

Inflorescence:

*Description.*—Rounded umbel of inconspicuous flowers subtended by showy bracts.

*Number of true flowers per inflorescence.*—50-100.

*Flowering season.*—June to early July, bracts persist through July in Mills River, N.C.

*Fragrance.*—None.

*Flower bud.*—Position: Terminal. Shape: Rounded. Texture: Pubescent. Color: Yellow-green (RHS 148C).

*Inflorescence diameter.*—Avg. 11 cm (10 to 12 cm).

*True flowers.*—Number per umbel: 50-100. Diameter: About 3 mm. Sepal color: Yellow-green (RHS 148C). Petal color: Yellow-green (RHS 148C). Number of pistils: 1. Number of stamens: 4.

*Perianth.*—Diameter at anthesis: Avg. 11 cm (9 to 11.5 cm). Height at anthesis: Avg. 1 cm (0.8 to 1.1 cm).

*Peduncle.*—Length: Avg. 7 cm (6 to 8 cm). Width: Avg. 1.15 mm (1 to 1.3 mm). Color: Yellow-Green (RHS 145A). Texture: glabrous to puberulent.

*Bracts (at anthesis).*—Number: 4. Shape: Elliptical. Apex: Acuminate. Length: Avg. 5.3 cm (4.3 to 6.3 cm). Width: Avg. 3.2 cm (2.4 to 3.4 cm). Surface texture: Glabrous, both sides. Color: White (RHS 155A), both upper and lower surfaces.

Fruit:

*Description.*—Drupe born on a pendulous stalk (Avg. 5 cm long), maturing in early fall.

*Shape.*—Globose.

*Diameter.*—Avg. 1.8 cm (range 1.5 to 2 cm).

*Color at maturity.*—Greyed-red (RHS 179A).

Seed:

*Shape.*—Elliptical.

*Length.*—Avg. 0.7 cm (range 0.5 to 0.8 cm).

*Width.*—Avg. 0.5 cm (range 0.3 to 0.6 cm).

*Color.*—Greyed-orange (RHS 165C).

Shoot and stem:

*Shoot length.*—Avg. 9 cm (range 4 to 15 cm).

*Shoot diameter.*—Avg. 3 cm (2 to 4 cm).

*Internode length.*—Avg. 3 cm (2 to 4 cm).

*Immature shoot texture (current year).*—Pubescent.

*Immature shoot color (current year).*—Grey-brown (RHS N199B).

*Mature stem texture (from prior year).*—Heavily lenticelled.

*Mature stem color (from prior year).*—Grey-brown (RHS N199B).

*Trunk diameter.*—8 cm at 30 cm above the soil level.

*Bark texture.*—Corky, lenticelled.

*Bark color.*—Grey-brown (RHS N199B).

Disease and insect resistance: No significant disease or insect pests have been observed to date.

Cold hardiness: At least USDA zone 6b; testing has not been completed in colder zones.

COMPARISON WITH COMMERCIAL CULTIVARS

Table 1 shows distinguishing characteristics between 'NCCE1' and 'Elsbry', parent of 'NCCE1', and 'First Choice'. 'NCCE1' is distinguished from 'Elsbry' and 'First Choice' in that 'NCCE1' has a narrow, pyramidal habit, shorter branch internodes, and larger inflorescences. 'NCCE1' also has greyed-purple winter foliage color, whereas *C. elliptica* 'Elsbry' and 'First Choice' have a greener winter foliage color.

TABLE 1

Comparison to commercial cultivars.

| | Taxa | | |
|---|---|---|---|
| Trait | *Cornus* 'NCCE1' | *Cornus* 'Elsbry' | *Cornus* 'First Choice' |
| Plant height | 4 m | 4 m | 4 m |
| Plant width | 1-1.3 m | 4 m | 4 m |
| Plant habit | Narrow, pyramidal | Rounded, spreading | Rounded, spreading |
| Branch internode length | Avg. 3 cm | Avg. 10.3 cm | Avg. 5.5 |
| Inflorescence diameter | Avg. 11 cm | Avg. 6.5 cm | Avg. 6.5 cm |
| Winter foliage color: Upper surface | Greyed-purple RHS 183A | Green RHS 137B with Greyed-purple margin RHS 183A | Green RHS 137B |

What is claimed is:

1. A new and distinct dogwood plant named 'NCCE1' substantially as illustrated and described herein.

* * * * *